(12) United States Patent
Trusty et al.

(10) Patent No.: US 8,496,574 B2
(45) Date of Patent: Jul. 30, 2013

(54) SELECTIVELY POSITIONABLE CAMERA FOR SURGICAL GUIDE TUBE ASSEMBLY

(75) Inventors: Robert M. Trusty, Cincinnati, OH (US); Gregory J. Bakos, Mason, OH (US); James T. Spivey, Cincinnati, OH (US); Omar J. Vakharia, Cincinnati, OH (US); Dashiell A. Birnkrant, Worcester, MA (US); John J. Elliott, Jr., Ashburnham, MA (US)

(73) Assignees: Ethicon Endo-Surgery, Inc., Cincinnati, OH (US); Karl Storz Endovision, Inc., Charlton, MA (US)

( * ) Notice: Subject to any disclaimer, the term of this patent is extended or adjusted under 35 U.S.C. 154(b) by 819 days.

(21) Appl. No.: 12/640,476

(22) Filed: Dec. 17, 2009

(65) Prior Publication Data

US 2011/0152612 A1    Jun. 23, 2011

(51) Int. Cl.
*A61B 1/04* (2006.01)
(52) U.S. Cl.
USPC ............................................ 600/114; 396/17
(58) Field of Classification Search
USPC .................. 600/114, 125; 396/17; 348/77
See application file for complete search history.

(56) References Cited

U.S. PATENT DOCUMENTS

| 645,576 | A | 3/1900 | Telsa |
|---|---|---|---|
| 649,621 | A | 5/1900 | Tesla |
| 787,412 | A | 4/1905 | Tesla |
| 1,039,354 | A | 9/1912 | Bonadio |
| 1,127,948 | A | 2/1915 | Wappler |
| 1,482,653 | A | 2/1924 | Lilly |
| 1,625,602 | A | 4/1927 | Gould et al. |
| 1,916,722 | A | 7/1933 | Ende |
| 2,028,635 | A | 1/1936 | Wappler |
| 2,031,682 | A | 2/1936 | Wappler et al. |
| 2,113,246 | A | 4/1938 | Wappler |
| 2,155,365 | A | 4/1939 | Rankin |
| 2,191,858 | A | 2/1940 | Moore |
| 2,196,620 | A | 4/1940 | Attarian |
| 2,388,137 | A | 10/1945 | Graumlich |
| 2,493,108 | A | 1/1950 | Casey, Jr. |

(Continued)

FOREIGN PATENT DOCUMENTS

| AU | 666310 B2 | 2/1996 |
|---|---|---|
| DE | 3008120 A1 | 9/1980 |

(Continued)

OTHER PUBLICATIONS

International Search Report and Written Opinion for PCT/US2010/060242, Mar. 23, 2011 (13 pages).

(Continued)

*Primary Examiner* — Christopher Mahoney

(57) ABSTRACT

A selectively positionable camera assembly for use in connection with a guide tube assembly that has a guide tube handle portion and at least one guide tube protruding therefrom. In various embodiments, the camera includes an elongated flexible camera portion that is sized to operably extend through at least one of the guide tubes of the guide tube assembly. A camera handle is operably coupled to the elongated flexible camera portion such that the handle is movably supported by at least a portion of the guide tube handle portion. At least one retainer is provided on the guide tube handle and/or the camera handle for releasably retaining the camera handle in any one of a plurality of orientations relative to the portion of the guide tube handle.

14 Claims, 6 Drawing Sheets

U.S. PATENT DOCUMENTS

| | | |
|---|---|---|
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,727,600 A | 2/1988 | Avakian |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,342,396 A | 8/1994 | Cook |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |

| | | | | | | |
|---|---|---|---|---|---|---|
| 5,356,408 A | 10/1994 | Rydell | | 5,569,243 A | 10/1996 | Kortenbach et al. |
| 5,360,428 A | 11/1994 | Hutchinson, Jr. | | 5,569,298 A | 10/1996 | Schnell |
| 5,364,408 A | 11/1994 | Gordon | | 5,571,090 A | 11/1996 | Sherts |
| 5,364,410 A | 11/1994 | Failla et al. | | 5,573,540 A | 11/1996 | Yoon |
| 5,366,466 A | 11/1994 | Christian et al. | | 5,578,030 A | 11/1996 | Levin |
| 5,366,467 A | 11/1994 | Lynch et al. | | 5,582,611 A | 12/1996 | Tsuruta et al. |
| 5,368,605 A | 11/1994 | Miller, Jr. | | 5,582,617 A | 12/1996 | Klieman et al. |
| 5,370,647 A | 12/1994 | Graber et al. | | 5,584,845 A | 12/1996 | Hart |
| 5,370,679 A | 12/1994 | Atlee, III | | 5,591,179 A | 1/1997 | Edelstein |
| 5,374,273 A | 12/1994 | Nakao et al. | | 5,591,205 A | 1/1997 | Fowler |
| 5,374,275 A | 12/1994 | Bradley et al. | | 5,593,420 A | 1/1997 | Eubanks, Jr et al. |
| 5,374,277 A | 12/1994 | Hassler | | 5,595,562 A | 1/1997 | Grier |
| 5,377,695 A | 1/1995 | An Haack | | 5,597,378 A | 1/1997 | Jervis |
| 5,383,877 A | 1/1995 | Clarke | | 5,601,573 A | 2/1997 | Fogelberg et al. |
| 5,383,888 A | 1/1995 | Zvenyatsky et al. | | 5,601,588 A | 2/1997 | Tonomura et al. |
| 5,386,817 A | 2/1995 | Jones | | 5,601,602 A | 2/1997 | Fowler |
| 5,387,259 A | 2/1995 | Davidson | | 5,604,531 A | 2/1997 | Iddan et al. |
| 5,391,174 A | 2/1995 | Weston | | 5,607,389 A | 3/1997 | Edwards et al. |
| 5,392,789 A | 2/1995 | Slater et al. | | 5,607,406 A | 3/1997 | Hernandez et al. |
| 5,395,386 A | 3/1995 | Slater | | 5,607,450 A | 3/1997 | Zvenyatsky et al. |
| 5,401,248 A | 3/1995 | Bencini | | 5,609,601 A | 3/1997 | Kolesa et al. |
| 5,403,328 A | 4/1995 | Shallman | | 5,613,975 A | 3/1997 | Christy |
| 5,403,342 A | 4/1995 | Tovey et al. | | 5,618,303 A | 4/1997 | Marlow et al. |
| 5,403,348 A | 4/1995 | Bonutti | | 5,620,415 A | 4/1997 | Lucey et al. |
| 5,405,073 A | 4/1995 | Porter | | 5,624,399 A | 4/1997 | Ackerman |
| 5,405,359 A | 4/1995 | Pierce | | 5,624,431 A | 4/1997 | Gerry et al. |
| 5,409,478 A | 4/1995 | Gerry et al. | | 5,626,578 A | 5/1997 | Tihon |
| 5,417,699 A | 5/1995 | Klein et al. | | 5,628,732 A | 5/1997 | Antoon, Jr. et al. |
| 5,423,821 A | 6/1995 | Pasque | | 5,630,782 A | 5/1997 | Adair |
| 5,433,721 A | 7/1995 | Hooven et al. | | 5,643,283 A | 7/1997 | Younker |
| 5,439,471 A | 8/1995 | Kerr | | 5,643,292 A | 7/1997 | Hart |
| 5,439,478 A | 8/1995 | Palmer | | 5,643,294 A | 7/1997 | Tovey et al. |
| 5,441,059 A | 8/1995 | Dannan | | 5,644,798 A | 7/1997 | Shah |
| 5,441,494 A | 8/1995 | Ortiz | | 5,645,083 A | 7/1997 | Essig et al. |
| 5,441,499 A | 8/1995 | Fritzsch | | 5,645,565 A | 7/1997 | Rudd et al. |
| 5,443,463 A | 8/1995 | Stern et al. | | 5,649,372 A | 7/1997 | Souza |
| 5,445,638 A | 8/1995 | Rydell et al. | | 5,653,677 A | 8/1997 | Okada et al. |
| 5,445,648 A | 8/1995 | Cook | | 5,653,690 A | 8/1997 | Booth et al. |
| 5,449,021 A | 9/1995 | Chikama | | 5,653,722 A | 8/1997 | Kieturakis |
| 5,454,827 A | 10/1995 | Aust et al. | | 5,657,755 A | 8/1997 | Desai |
| 5,456,667 A | 10/1995 | Ham et al. | | 5,662,621 A | 9/1997 | Lafontaine |
| 5,456,684 A | 10/1995 | Schmidt et al. | | 5,662,663 A | 9/1997 | Shallman |
| 5,458,131 A | 10/1995 | Wilk | | 5,667,527 A | 9/1997 | Cook |
| 5,458,583 A | 10/1995 | McNeely et al. | | 5,669,875 A | 9/1997 | van Eerdenburg |
| 5,460,168 A | 10/1995 | Masubuchi et al. | | 5,681,324 A | 10/1997 | Kammerer et al. |
| 5,460,629 A | 10/1995 | Shlain et al. | | 5,681,330 A | 10/1997 | Hughett et al. |
| 5,462,561 A | 10/1995 | Voda | | 5,685,820 A | 11/1997 | Riek et al. |
| 5,465,731 A | 11/1995 | Bell et al. | | 5,690,606 A | 11/1997 | Slotman |
| 5,467,763 A | 11/1995 | McMahon et al. | | 5,690,656 A | 11/1997 | Cope et al. |
| 5,468,250 A | 11/1995 | Paraschac et al. | | 5,690,660 A | 11/1997 | Kauker et al. |
| 5,470,308 A | 11/1995 | Edwards et al. | | 5,695,448 A | 12/1997 | Kimura et al. |
| 5,470,320 A | 11/1995 | Tiefenbrun et al. | | 5,695,505 A | 12/1997 | Yoon |
| 5,478,347 A | 12/1995 | Aranyi | | 5,695,511 A | 12/1997 | Cano et al. |
| 5,478,352 A | 12/1995 | Fowler | | 5,700,275 A | 12/1997 | Bell et al. |
| 5,480,404 A | 1/1996 | Kammerer et al. | | 5,702,438 A | 12/1997 | Avitall |
| 5,482,054 A | 1/1996 | Slater et al. | | 5,704,892 A | 1/1998 | Adair |
| 5,484,451 A | 1/1996 | Akopov et al. | | 5,709,708 A | 1/1998 | Thal |
| 5,489,256 A | 2/1996 | Adair | | 5,711,921 A | 1/1998 | Langford |
| 5,496,347 A | 3/1996 | Hashiguchi et al. | | 5,716,326 A | 2/1998 | Dannan |
| 5,499,990 A | 3/1996 | Schülken et al. | | 5,716,375 A | 2/1998 | Fowler |
| 5,499,992 A | 3/1996 | Meade et al. | | 5,728,094 A | 3/1998 | Edwards |
| 5,501,692 A | 3/1996 | Riza | | 5,730,740 A | 3/1998 | Wales et al. |
| 5,503,616 A | 4/1996 | Jones | | 5,735,849 A | 4/1998 | Baden et al. |
| 5,505,686 A | 4/1996 | Willis et al. | | 5,741,234 A | 4/1998 | Aboul-Hosn |
| 5,507,755 A | 4/1996 | Gresl et al. | | 5,741,278 A | 4/1998 | Stevens |
| 5,511,564 A | 4/1996 | Wilk | | 5,741,285 A | 4/1998 | McBrayer et al. |
| 5,514,157 A | 5/1996 | Nicholas et al. | | 5,741,429 A | 4/1998 | Donadio, III et al. |
| 5,518,501 A | 5/1996 | Oneda et al. | | 5,743,456 A | 4/1998 | Jones et al. |
| 5,522,829 A | 6/1996 | Michalos | | 5,746,759 A | 5/1998 | Meade et al. |
| 5,522,830 A | 6/1996 | Aranyi | | 5,749,826 A | 5/1998 | Faulkner |
| 5,527,321 A | 6/1996 | Hinchliffe | | 5,749,881 A | 5/1998 | Sackier et al. |
| 5,536,248 A | 7/1996 | Weaver et al. | | 5,749,889 A | 5/1998 | Bacich et al. |
| 5,538,509 A | 7/1996 | Dunlap et al. | | 5,752,951 A | 5/1998 | Yanik |
| 5,540,648 A | 7/1996 | Yoon | | 5,755,731 A | 5/1998 | Grinberg |
| 5,549,637 A | 8/1996 | Crainich | | 5,766,167 A | 6/1998 | Eggers et al. |
| 5,554,151 A | 9/1996 | Hinchliffe | | 5,766,170 A | 6/1998 | Eggers |
| 5,555,883 A | 9/1996 | Avitall | | 5,766,205 A | 6/1998 | Zvenyatsky et al. |
| 5,558,133 A | 9/1996 | Bortoli et al. | | 5,769,849 A | 6/1998 | Eggers |
| 5,562,693 A | 10/1996 | Devlin et al. | | 5,779,701 A | 7/1998 | McBrayer et al. |

| | | | | | |
|---|---|---|---|---|---|
| 5,779,716 A | 7/1998 | Cano et al. | 5,976,074 A | 11/1999 | Moriyama |
| 5,779,727 A | 7/1998 | Orejola | 5,976,075 A | 11/1999 | Beane et al. |
| 5,782,859 A | 7/1998 | Nicholas et al. | 5,976,130 A | 11/1999 | McBrayer et al. |
| 5,782,861 A | 7/1998 | Cragg et al. | 5,976,131 A | 11/1999 | Guglielmi et al. |
| 5,782,866 A | 7/1998 | Wenstrom, Jr. | 5,980,539 A | 11/1999 | Kontos |
| 5,791,022 A | 8/1998 | Bohman | 5,980,556 A | 11/1999 | Giordano et al. |
| 5,792,113 A | 8/1998 | Kramer et al. | 5,984,938 A | 11/1999 | Yoon |
| 5,792,153 A | 8/1998 | Swain et al. | 5,984,939 A | 11/1999 | Yoon |
| 5,792,165 A | 8/1998 | Klieman et al. | 5,984,950 A | 11/1999 | Cragg et al. |
| 5,797,835 A | 8/1998 | Green | 5,989,182 A | 11/1999 | Hori et al. |
| 5,797,928 A | 8/1998 | Kogasaka | 5,993,447 A | 11/1999 | Blewett et al. |
| 5,797,939 A | 8/1998 | Yoon | 5,993,474 A | 11/1999 | Ouchi |
| 5,797,941 A | 8/1998 | Schulze et al. | 5,997,555 A | 12/1999 | Kontos |
| 5,797,959 A | 8/1998 | Castro et al. | 6,001,120 A | 12/1999 | Levin |
| 5,803,903 A | 9/1998 | Athas et al. | 6,004,269 A | 12/1999 | Crowley et al. |
| 5,808,665 A | 9/1998 | Green | 6,004,330 A | 12/1999 | Middleman et al. |
| 5,810,806 A | 9/1998 | Ritchart et al. | 6,007,566 A | 12/1999 | Wenstrom, Jr. |
| 5,810,849 A | 9/1998 | Kontos | 6,010,515 A | 1/2000 | Swain et al. |
| 5,810,865 A | 9/1998 | Koscher et al. | 6,012,494 A | 1/2000 | Balazs |
| 5,810,876 A | 9/1998 | Kelleher | 6,017,356 A | 1/2000 | Frederick et al. |
| 5,810,877 A | 9/1998 | Roth et al. | 6,019,770 A | 2/2000 | Christoudias |
| 5,813,976 A | 9/1998 | Filipi et al. | 6,024,708 A | 2/2000 | Bales et al. |
| 5,814,058 A | 9/1998 | Carlson et al. | 6,024,747 A | 2/2000 | Kontos |
| 5,817,061 A | 10/1998 | Goodwin et al. | 6,027,522 A | 2/2000 | Palmer |
| 5,817,107 A | 10/1998 | Schaller | 6,030,365 A | 2/2000 | Laufer |
| 5,817,119 A | 10/1998 | Klieman et al. | 6,030,384 A | 2/2000 | Nezhat |
| 5,819,736 A | 10/1998 | Avny et al. | 6,030,634 A | 2/2000 | Wu et al. |
| 5,823,947 A | 10/1998 | Yoon et al. | 6,033,399 A | 3/2000 | Gines |
| 5,824,071 A | 10/1998 | Nelson et al. | 6,036,685 A | 3/2000 | Mueller |
| 5,827,276 A | 10/1998 | LeVeen et al. | 6,053,927 A | 4/2000 | Hamas |
| 5,827,281 A | 10/1998 | Levin | 6,053,937 A | 4/2000 | Edwards et al. |
| 5,827,299 A | 10/1998 | Thomason et al. | 6,066,160 A | 5/2000 | Colvin et al. |
| 5,827,323 A | 10/1998 | Klieman et al. | 6,068,603 A | 5/2000 | Suzuki |
| 5,830,231 A | 11/1998 | Geiges, Jr. | 6,068,629 A | 5/2000 | Haissaguerre et al. |
| 5,833,603 A | 11/1998 | Kovacs et al. | 6,071,233 A | 6/2000 | Ishikawa et al. |
| 5,833,700 A | 11/1998 | Fogelberg et al. | 6,074,408 A | 6/2000 | Freeman |
| 5,833,703 A | 11/1998 | Manushakian | 6,086,530 A | 7/2000 | Mack |
| 5,836,960 A | 11/1998 | Kolesa et al. | 6,090,105 A | 7/2000 | Zepeda et al. |
| 5,843,017 A | 12/1998 | Yoon | 6,090,108 A | 7/2000 | McBrayer et al. |
| 5,843,121 A | 12/1998 | Yoon | 6,090,129 A | 7/2000 | Ouchi |
| 5,849,022 A | 12/1998 | Sakashita et al. | 6,096,046 A | 8/2000 | Weiss |
| 5,853,374 A | 12/1998 | Hart et al. | 6,102,926 A | 8/2000 | Tartaglia et al. |
| 5,855,585 A | 1/1999 | Kontos | 6,106,473 A | 8/2000 | Violante et al. |
| 5,860,913 A | 1/1999 | Yamaya et al. | 6,109,852 A | 8/2000 | Shahinpoor et al. |
| 5,860,995 A | 1/1999 | Berkelaar | 6,110,154 A | 8/2000 | Shimomura et al. |
| 5,868,762 A | 2/1999 | Cragg et al. | 6,110,183 A | 8/2000 | Cope |
| 5,876,411 A | 3/1999 | Kontos | 6,113,593 A | 9/2000 | Tu et al. |
| 5,882,331 A | 3/1999 | Sasaki | 6,117,144 A | 9/2000 | Nobles et al. |
| 5,882,344 A | 3/1999 | Stouder, Jr. | 6,117,158 A | 9/2000 | Measamer et al. |
| 5,893,846 A | 4/1999 | Bales et al. | 6,139,555 A | 10/2000 | Hart et al. |
| 5,893,874 A | 4/1999 | Bourque et al. | 6,141,037 A | 10/2000 | Upton et al. |
| 5,893,875 A | 4/1999 | O'Connor et al. | 6,146,391 A | 11/2000 | Cigaina |
| 5,897,487 A | 4/1999 | Ouchi | 6,148,222 A | 11/2000 | Ramsey, III |
| 5,899,919 A | 5/1999 | Eubanks, Jr. et al. | 6,149,653 A | 11/2000 | Deslauriers |
| 5,902,254 A | 5/1999 | Magram | 6,149,662 A | 11/2000 | Pugliesi et al. |
| 5,904,702 A | 5/1999 | Ek et al. | 6,152,920 A | 11/2000 | Thompson et al. |
| 5,908,420 A | 6/1999 | Parins et al. | 6,156,006 A | 12/2000 | Brosens et al. |
| 5,908,429 A | 6/1999 | Yoon | 6,159,200 A | 12/2000 | Verdura et al. |
| 5,911,737 A | 6/1999 | Lee et al. | 6,165,175 A | 12/2000 | Wampler et al. |
| 5,916,146 A | 6/1999 | Allotta et al. | 6,165,184 A | 12/2000 | Verdura et al. |
| 5,916,147 A | 6/1999 | Boury | 6,168,570 B1 | 1/2001 | Ferrera |
| 5,921,993 A | 7/1999 | Yoon | 6,168,605 B1 | 1/2001 | Measamer et al. |
| 5,921,997 A | 7/1999 | Fogelberg et al. | 6,169,269 B1 | 1/2001 | Maynard |
| 5,922,008 A | 7/1999 | Gimpelson | 6,170,130 B1 | 1/2001 | Hamilton et al. |
| 5,925,052 A | 7/1999 | Simmons | 6,179,776 B1 | 1/2001 | Adams et al. |
| 5,928,255 A | 7/1999 | Meade et al. | 6,179,832 B1 | 1/2001 | Jones et al. |
| 5,928,266 A | 7/1999 | Kontos | 6,179,837 B1 | 1/2001 | Hooven |
| 5,936,536 A | 8/1999 | Morris | 6,183,420 B1 | 2/2001 | Douk et al. |
| 5,944,718 A | 8/1999 | Austin et al. | 6,190,353 B1 | 2/2001 | Makower et al. |
| 5,951,547 A | 9/1999 | Gough et al. | 6,190,383 B1 | 2/2001 | Schmaltz et al. |
| 5,951,549 A | 9/1999 | Richardson et al. | 6,190,384 B1 | 2/2001 | Ouchi |
| 5,954,720 A | 9/1999 | Wilson et al. | 6,190,399 B1 | 2/2001 | Palmer et al. |
| 5,954,731 A | 9/1999 | Yoon | 6,203,533 B1 | 3/2001 | Ouchi |
| 5,957,936 A | 9/1999 | Yoon et al. | 6,206,872 B1 | 3/2001 | Lafond et al. |
| 5,957,943 A | 9/1999 | Vaitekunas | 6,206,877 B1 | 3/2001 | Kese et al. |
| 5,957,953 A | 9/1999 | DiPoto et al. | 6,206,904 B1 | 3/2001 | Ouchi |
| 5,964,782 A | 10/1999 | Lafontaine et al. | 6,210,409 B1 | 4/2001 | Ellman et al. |
| 5,971,995 A | 10/1999 | Rousseau | 6,214,007 B1 | 4/2001 | Anderson |
| 5,972,002 A | 10/1999 | Bark et al. | 6,214,028 B1 | 4/2001 | Yoon et al. |

| | | |
|---|---|---|
| 6,216,043 B1 | 4/2001 | Swanson et al. |
| 6,228,096 B1 | 5/2001 | Marchand |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,527,782 B2 | 3/2003 | Hogg et al. |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,554,766 B2 | 4/2003 | Maeda et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B1 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,673,092 B1 | 1/2004 | Bacher |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |

| Patent | Type | Date | Inventor |
|---|---|---|---|
| 6,808,491 | B2 | 10/2004 | Kortenbach et al. |
| 6,817,974 | B2 | 11/2004 | Cooper et al. |
| 6,818,007 | B1 | 11/2004 | Dampney et al. |
| 6,824,548 | B2 | 11/2004 | Smith et al. |
| 6,830,545 | B2 * | 12/2004 | Bendall .......... 600/114 |
| 6,836,688 | B2 | 12/2004 | Ingle et al. |
| 6,837,847 | B2 | 1/2005 | Ewers et al. |
| 6,840,246 | B2 | 1/2005 | Downing |
| 6,840,938 | B1 | 1/2005 | Morley et al. |
| 6,843,794 | B2 | 1/2005 | Sixto, Jr. et al. |
| 6,861,250 | B1 | 3/2005 | Cole et al. |
| 6,866,627 | B2 | 3/2005 | Nozue |
| 6,866,628 | B2 | 3/2005 | Goodman et al. |
| 6,869,394 | B2 | 3/2005 | Ishibiki |
| 6,878,106 | B1 | 4/2005 | Herrmann |
| 6,878,110 | B2 | 4/2005 | Yang et al. |
| 6,881,213 | B2 | 4/2005 | Ryan et al. |
| 6,881,216 | B2 | 4/2005 | Di Caprio et al. |
| 6,884,213 | B2 | 4/2005 | Raz et al. |
| 6,887,255 | B2 | 5/2005 | Shimm |
| 6,889,089 | B2 | 5/2005 | Behl et al. |
| 6,896,683 | B1 | 5/2005 | Gadberry et al. |
| 6,896,692 | B2 | 5/2005 | Ginn et al. |
| 6,899,710 | B2 | 5/2005 | Hooven |
| 6,908,427 | B2 | 6/2005 | Fleener et al. |
| 6,908,476 | B2 | 6/2005 | Jud et al. |
| 6,913,613 | B2 | 7/2005 | Schwarz et al. |
| 6,916,284 | B2 | 7/2005 | Moriyama |
| 6,918,871 | B2 | 7/2005 | Schulze |
| 6,918,908 | B2 | 7/2005 | Bonner et al. |
| 6,926,725 | B2 | 8/2005 | Cooke et al. |
| 6,932,810 | B2 | 8/2005 | Ryan |
| 6,932,824 | B1 | 8/2005 | Roop et al. |
| 6,932,827 | B2 | 8/2005 | Cole |
| 6,932,834 | B2 | 8/2005 | Lizardi et al. |
| 6,936,003 | B2 | 8/2005 | Iddan |
| 6,939,327 | B2 | 9/2005 | Hall et al. |
| 6,942,613 | B2 | 9/2005 | Ewers et al. |
| 6,944,490 | B1 | 9/2005 | Chow |
| 6,945,472 | B2 | 9/2005 | Wuttke et al. |
| 6,945,979 | B2 | 9/2005 | Kortenbach et al. |
| 6,955,683 | B2 | 10/2005 | Bonutti |
| 6,958,035 | B2 | 10/2005 | Friedman et al. |
| 6,960,162 | B2 | 11/2005 | Saadat et al. |
| 6,960,163 | B2 | 11/2005 | Ewers et al. |
| 6,962,587 | B2 | 11/2005 | Johnson et al. |
| 6,964,662 | B2 | 11/2005 | Kidooka |
| 6,966,909 | B2 | 11/2005 | Marshall et al. |
| 6,966,919 | B2 | 11/2005 | Sixto, Jr. et al. |
| 6,967,462 | B1 | 11/2005 | Landis |
| 6,971,988 | B2 | 12/2005 | Orban, III |
| 6,972,017 | B2 | 12/2005 | Smith et al. |
| 6,974,411 | B2 | 12/2005 | Belson |
| 6,976,992 | B2 | 12/2005 | Sachatello et al. |
| 6,984,203 | B2 | 1/2006 | Tartaglia et al. |
| 6,984,205 | B2 | 1/2006 | Gazdzinski |
| 6,986,774 | B2 | 1/2006 | Middleman et al. |
| 6,988,987 | B2 | 1/2006 | Ishikawa et al. |
| 6,989,028 | B2 | 1/2006 | Lashinski et al. |
| 6,991,627 | B2 | 1/2006 | Madhani et al. |
| 6,991,631 | B2 | 1/2006 | Woloszko et al. |
| 6,994,708 | B2 | 2/2006 | Manzo |
| 6,997,931 | B2 | 2/2006 | Sauer et al. |
| 7,000,818 | B2 | 2/2006 | Shelton, IV et al. |
| 7,001,341 | B2 | 2/2006 | Gellman et al. |
| 7,008,375 | B2 | 3/2006 | Weisel |
| 7,008,419 | B2 | 3/2006 | Shadduck |
| 7,009,634 | B2 | 3/2006 | Iddan et al. |
| 7,010,340 | B2 | 3/2006 | Scarantino et al. |
| 7,020,531 | B1 | 3/2006 | Colliou et al. |
| 7,025,580 | B2 | 4/2006 | Heagy et al. |
| 7,029,435 | B2 | 4/2006 | Nakao |
| 7,029,438 | B2 | 4/2006 | Morin et al. |
| 7,029,450 | B2 | 4/2006 | Gellman |
| 7,032,600 | B2 | 4/2006 | Fukuda et al. |
| 7,035,680 | B2 | 4/2006 | Partridge et al. |
| 7,037,290 | B2 | 5/2006 | Gardeski et al. |
| 7,041,052 | B2 | 5/2006 | Saadat et al. |
| 7,052,489 | B2 | 5/2006 | Griego et al. |
| 7,060,024 | B2 | 6/2006 | Long et al. |
| 7,060,025 | B2 | 6/2006 | Long et al. |
| 7,063,697 | B2 | 6/2006 | Slater |
| 7,063,715 | B2 | 6/2006 | Onuki et al. |
| 7,066,879 | B2 | 6/2006 | Fowler et al. |
| 7,066,936 | B2 | 6/2006 | Ryan |
| 7,070,602 | B2 | 7/2006 | Smith et al. |
| 7,076,305 | B2 | 7/2006 | Imran et al. |
| 7,083,618 | B2 | 8/2006 | Couture et al. |
| 7,083,620 | B2 | 8/2006 | Jahns et al. |
| 7,083,629 | B2 | 8/2006 | Weller et al. |
| 7,083,635 | B2 | 8/2006 | Ginn |
| 7,087,071 | B2 | 8/2006 | Nicholas et al. |
| 7,088,923 | B2 | 8/2006 | Haruyama |
| 7,090,673 | B2 | 8/2006 | Dycus et al. |
| 7,090,683 | B2 | 8/2006 | Brock et al. |
| 7,090,685 | B2 | 8/2006 | Kortenbach et al. |
| 7,093,518 | B2 | 8/2006 | Gmeilbauer |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,105,000 | B2 | 9/2006 | McBrayer |
| 7,105,005 | B2 | 9/2006 | Blake |
| 7,108,696 | B2 | 9/2006 | Daniel et al. |
| 7,108,703 | B2 | 9/2006 | Danitz et al. |
| 7,112,208 | B2 | 9/2006 | Morris et al. |
| 7,115,092 | B2 | 10/2006 | Park et al. |
| 7,115,124 | B1 | 10/2006 | Xiao |
| 7,117,703 | B2 | 10/2006 | Kato et al. |
| 7,118,531 | B2 | 10/2006 | Krill |
| 7,118,578 | B2 | 10/2006 | West, Jr. et al. |
| 7,118,587 | B2 | 10/2006 | Dycus et al. |
| 7,128,708 | B2 | 10/2006 | Saadat et al. |
| RE39,415 | E | 11/2006 | Bales et al. |
| 7,131,978 | B2 | 11/2006 | Sancoff et al. |
| 7,131,979 | B2 | 11/2006 | DiCarlo et al. |
| 7,131,980 | B1 | 11/2006 | Field et al. |
| 7,137,980 | B2 | 11/2006 | Buysse et al. |
| 7,137,981 | B2 | 11/2006 | Long |
| 7,146,984 | B2 | 12/2006 | Stack et al. |
| 7,147,650 | B2 | 12/2006 | Lee |
| 7,150,097 | B2 | 12/2006 | Sremcich et al. |
| 7,150,655 | B2 | 12/2006 | Mastrototaro et al. |
| 7,150,750 | B2 | 12/2006 | Damarati |
| 7,152,488 | B2 | 12/2006 | Hedrich et al. |
| 7,153,321 | B2 | 12/2006 | Andrews |
| 7,160,296 | B2 | 1/2007 | Pearson et al. |
| 7,163,525 | B2 | 1/2007 | Franer |
| 7,172,714 | B2 | 2/2007 | Jacobson |
| 7,179,254 | B2 | 2/2007 | Pendekanti et al. |
| 7,188,627 | B2 | 3/2007 | Nelson et al. |
| 7,195,612 | B2 | 3/2007 | Van Sloten et al. |
| 7,195,631 | B2 | 3/2007 | Dumbauld |
| 7,204,820 | B2 | 4/2007 | Akahoshi |
| 7,208,005 | B2 | 4/2007 | Frecker et al. |
| 7,211,092 | B2 | 5/2007 | Hughett |
| 7,220,227 | B2 | 5/2007 | Sasaki et al. |
| 7,223,272 | B2 | 5/2007 | Francese et al. |
| 7,229,438 | B2 | 6/2007 | Young |
| 7,232,414 | B2 | 6/2007 | Gonzalez |
| 7,232,445 | B2 | 6/2007 | Kortenbach et al. |
| 7,235,089 | B1 | 6/2007 | McGuckin, Jr. |
| 7,241,290 | B2 | 7/2007 | Doyle et al. |
| 7,244,228 | B2 | 7/2007 | Lubowski |
| 7,250,027 | B2 | 7/2007 | Barry |
| 7,252,660 | B2 | 8/2007 | Kunz |
| 7,255,675 | B2 | 8/2007 | Gertner et al. |
| 7,261,725 | B2 | 8/2007 | Binmoeller |
| 7,270,663 | B2 | 9/2007 | Nakao |
| 7,291,127 | B2 | 11/2007 | Eidenschink |
| 7,294,139 | B1 | 11/2007 | Gengler |
| 7,301,250 | B2 | 11/2007 | Cassel |
| 7,306,597 | B2 | 12/2007 | Manzo |
| 7,308,828 | B2 | 12/2007 | Hashimoto |
| 7,318,802 | B2 | 1/2008 | Suzuki et al. |
| 7,320,695 | B2 | 1/2008 | Carroll |
| 7,322,934 | B2 | 1/2008 | Miyake et al. |
| 7,323,006 | B2 | 1/2008 | Andreas et al. |
| 7,329,256 | B2 | 2/2008 | Johnson et al. |

| Patent | Date | Name |
|---|---|---|
| 7,329,257 B2 | 2/2008 | Kanehira et al. |
| 7,329,383 B2 | 2/2008 | Stinson |
| 7,335,220 B2 | 2/2008 | Khosravi et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,390,324 B2 | 6/2008 | Whalen et al. |
| 7,393,222 B2 | 7/2008 | Asakura |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,476,237 B2 | 1/2009 | Taniguchi et al. |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,674,259 B2 | 3/2010 | Shadduck |
| 7,678,043 B2 | 3/2010 | Gilad |
| 7,684,599 B2 | 3/2010 | Horn et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,771,416 B2 | 8/2010 | Spivey et al. |
| 7,771,437 B2 | 8/2010 | Hogg et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,475 B2 | 9/2010 | Hess et al. |
| 7,798,386 B2 | 9/2010 | Schall et al. |
| 7,815,662 B2 | 10/2010 | Spivey et al. |
| 7,828,186 B2 | 11/2010 | Wales |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,879,004 B2 | 2/2011 | Seibel et al. |
| 7,892,220 B2 | 2/2011 | Faller et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,927,271 B2 | 4/2011 | Dimitriou et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,034,046 B2 | 10/2011 | Eidenschink |
| 8,048,067 B2 | 11/2011 | Davalos et al. |
| 8,057,510 B2 | 11/2011 | Ginn et al. |
| 8,062,311 B2 | 11/2011 | Litscher et al. |
| 8,066,632 B2 | 11/2011 | Dario et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,118,821 B2 | 2/2012 | Mouw |
| 8,147,424 B2 | 4/2012 | Kassab et al. |
| 8,157,813 B2 | 4/2012 | Ko et al. |
| 8,182,414 B2 | 5/2012 | Handa et al. |
| 8,303,581 B2 | 11/2012 | Arts et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |

| | | |
|---|---|---|
| 2002/0183591 A1 | 12/2002 | Matsuura et al. |
| 2003/0014090 A1 | 1/2003 | Abrahamson |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |

| | | | | | | |
|---|---|---|---|---|---|---|
| 2006/0058582 A1 | 3/2006 | Maahs et al. | | 2007/0010801 A1 | 1/2007 | Chen et al. |
| 2006/0058776 A1 | 3/2006 | Bilsbury | | 2007/0015965 A1 | 1/2007 | Cox et al. |
| 2006/0064083 A1 | 3/2006 | Khalaj et al. | | 2007/0016225 A1 | 1/2007 | Nakao |
| 2006/0069396 A1 | 3/2006 | Meade et al. | | 2007/0032700 A1 | 2/2007 | Fowler et al. |
| 2006/0069424 A1 | 3/2006 | Acosta et al. | | 2007/0032701 A1 | 2/2007 | Fowler et al. |
| 2006/0069425 A1 | 3/2006 | Hillis et al. | | 2007/0043261 A1 | 2/2007 | Watanabe et al. |
| 2006/0069429 A1 | 3/2006 | Spence et al. | | 2007/0043345 A1 | 2/2007 | Davalos et al. |
| 2006/0074413 A1 | 4/2006 | Behzadian | | 2007/0049800 A1 | 3/2007 | Boulais |
| 2006/0079890 A1 | 4/2006 | Guerra | | 2007/0049902 A1 | 3/2007 | Griffin et al. |
| 2006/0089528 A1 | 4/2006 | Tartaglia et al. | | 2007/0051375 A1 | 3/2007 | Milliman |
| 2006/0095031 A1 | 5/2006 | Ormsby | | 2007/0060880 A1 | 3/2007 | Gregorich et al. |
| 2006/0095060 A1 | 5/2006 | Mayenberger et al. | | 2007/0066869 A1 | 3/2007 | Hoffman |
| 2006/0100687 A1 | 5/2006 | Fahey et al. | | 2007/0067017 A1 | 3/2007 | Trapp |
| 2006/0106423 A1 | 5/2006 | Weisel et al. | | 2007/0073102 A1 | 3/2007 | Matsuno et al. |
| 2006/0111209 A1 | 5/2006 | Hinman et al. | | 2007/0073269 A1 | 3/2007 | Becker |
| 2006/0111210 A1 | 5/2006 | Hinman et al. | | 2007/0079924 A1 | 4/2007 | Saadat et al. |
| 2006/0111704 A1 | 5/2006 | Brenneman et al. | | 2007/0083195 A1 | 4/2007 | Werneth et al. |
| 2006/0129166 A1 | 6/2006 | Lavelle | | 2007/0088370 A1 | 4/2007 | Kahle et al. |
| 2006/0135962 A1 | 6/2006 | Kick et al. | | 2007/0100375 A1 | 5/2007 | Mikkaichi et al. |
| 2006/0135971 A1 | 6/2006 | Swanstrom et al. | | 2007/0100376 A1 | 5/2007 | Mikkaichi et al. |
| 2006/0135984 A1 | 6/2006 | Kramer et al. | | 2007/0106118 A1 | 5/2007 | Moriyama |
| 2006/0142644 A1 | 6/2006 | Mulac et al. | | 2007/0106317 A1 | 5/2007 | Shelton, IV et al. |
| 2006/0142652 A1 | 6/2006 | Keenan | | 2007/0112251 A1 | 5/2007 | Nakhuda |
| 2006/0142790 A1 | 6/2006 | Gertner | | 2007/0112331 A1 | 5/2007 | Weber et al. |
| 2006/0142798 A1 | 6/2006 | Holman et al. | | 2007/0112342 A1 | 5/2007 | Pearson et al. |
| 2006/0149131 A1 | 7/2006 | Or | | 2007/0112383 A1 | 5/2007 | Conlon et al. |
| 2006/0149132 A1 | 7/2006 | Iddan | | 2007/0112384 A1 | 5/2007 | Conlon et al. |
| 2006/0149135 A1 | 7/2006 | Paz | | 2007/0112385 A1 | 5/2007 | Conlon |
| 2006/0161190 A1 | 7/2006 | Gadberry et al. | | 2007/0112417 A1 | 5/2007 | Shanley et al. |
| 2006/0167416 A1 | 7/2006 | Mathis et al. | | 2007/0112425 A1 | 5/2007 | Schaller et al. |
| 2006/0167482 A1 | 7/2006 | Swain et al. | | 2007/0118115 A1 | 5/2007 | Artale et al. |
| 2006/0178560 A1 | 8/2006 | Saadat et al. | | 2007/0123840 A1 | 5/2007 | Cox |
| 2006/0183975 A1 | 8/2006 | Saadat et al. | | 2007/0129605 A1 | 6/2007 | Schaaf |
| 2006/0184161 A1 | 8/2006 | Maahs et al. | | 2007/0129719 A1 | 6/2007 | Kendale et al. |
| 2006/0189844 A1 | 8/2006 | Tien | | 2007/0129760 A1 | 6/2007 | Demarais et al. |
| 2006/0189845 A1 | 8/2006 | Maahs et al. | | 2007/0135709 A1 | 6/2007 | Rioux et al. |
| 2006/0190027 A1 | 8/2006 | Downey | | 2007/0135803 A1 | 6/2007 | Belson |
| 2006/0195084 A1 | 8/2006 | Slater | | 2007/0142706 A1 | 6/2007 | Matsui et al. |
| 2006/0200005 A1 | 9/2006 | Bjork et al. | | 2007/0142710 A1 | 6/2007 | Yokoi et al. |
| 2006/0200121 A1 | 9/2006 | Mowery | | 2007/0142780 A1 | 6/2007 | Van Lue |
| 2006/0200169 A1 | 9/2006 | Sniffin | | 2007/0154460 A1 | 7/2007 | Kraft et al. |
| 2006/0200170 A1 | 9/2006 | Aranyi | | 2007/0156028 A1 | 7/2007 | Van Lue et al. |
| 2006/0200199 A1 | 9/2006 | Bonutti et al. | | 2007/0156127 A1 | 7/2007 | Rioux et al. |
| 2006/0217665 A1 | 9/2006 | Prosek | | 2007/0161855 A1 | 7/2007 | Mikkaichi et al. |
| 2006/0217697 A1 | 9/2006 | Lau et al. | | 2007/0162101 A1 | 7/2007 | Burgermeister et al. |
| 2006/0217742 A1 | 9/2006 | Messerly et al. | | 2007/0167901 A1 | 7/2007 | Herrig et al. |
| 2006/0217743 A1 | 9/2006 | Messerly et al. | | 2007/0173691 A1 | 7/2007 | Yokoi et al. |
| 2006/0229639 A1 | 10/2006 | Whitfield | | 2007/0173869 A1 | 7/2007 | Gannoe et al. |
| 2006/0229640 A1 | 10/2006 | Whitfield | | 2007/0173870 A2 | 7/2007 | Zacharias |
| 2006/0237022 A1 | 10/2006 | Chen et al. | | 2007/0173872 A1 | 7/2007 | Neuenfeldt |
| 2006/0237023 A1 | 10/2006 | Cox et al. | | 2007/0179525 A1 | 8/2007 | Frecker et al. |
| 2006/0241570 A1 | 10/2006 | Wilk | | 2007/0179530 A1 | 8/2007 | Tieu et al. |
| 2006/0247500 A1 | 11/2006 | Voegele et al. | | 2007/0197865 A1 | 8/2007 | Miyake et al. |
| 2006/0247576 A1 | 11/2006 | Poncet | | 2007/0198057 A1 | 8/2007 | Gelbart et al. |
| 2006/0247673 A1 | 11/2006 | Voegele et al. | | 2007/0203398 A1 | 8/2007 | Bonadio et al. |
| 2006/0253004 A1 | 11/2006 | Frisch et al. | | 2007/0203487 A1 | 8/2007 | Sugita |
| 2006/0253039 A1 | 11/2006 | McKenna et al. | | 2007/0208336 A1 | 9/2007 | Kim et al. |
| 2006/0258907 A1 | 11/2006 | Stefanchik et al. | | 2007/0208364 A1 | 9/2007 | Smith et al. |
| 2006/0258908 A1 | 11/2006 | Stefanchik et al. | | 2007/0213754 A1 | 9/2007 | Mikkaichi et al. |
| 2006/0258910 A1 | 11/2006 | Stefanchik et al. | | 2007/0225554 A1 | 9/2007 | Maseda et al. |
| 2006/0258954 A1 | 11/2006 | Timberlake et al. | | 2007/0233040 A1 | 10/2007 | Macnamara et al. |
| 2006/0258955 A1 | 11/2006 | Hoffman et al. | | 2007/0244358 A1 | 10/2007 | Lee |
| 2006/0259010 A1 | 11/2006 | Stefanchik et al. | | 2007/0250038 A1 | 10/2007 | Boulais |
| 2006/0259073 A1 | 11/2006 | Miyamoto et al. | | 2007/0250057 A1 | 10/2007 | Nobis et al. |
| 2006/0264752 A1 | 11/2006 | Rubinsky et al. | | 2007/0255096 A1 | 11/2007 | Stefanchik et al. |
| 2006/0264904 A1 | 11/2006 | Kerby et al. | | 2007/0255100 A1 | 11/2007 | Barlow et al. |
| 2006/0264930 A1 | 11/2006 | Nishimura | | 2007/0255273 A1 | 11/2007 | Fernandez et al. |
| 2006/0270902 A1 | 11/2006 | Igarashi et al. | | 2007/0255303 A1 | 11/2007 | Bakos et al. |
| 2006/0271042 A1 | 11/2006 | Latterell et al. | | 2007/0255306 A1 | 11/2007 | Conlon et al. |
| 2006/0271102 A1 | 11/2006 | Bosshard et al. | | 2007/0260112 A1 | 11/2007 | Rahmani |
| 2006/0276835 A1 | 12/2006 | Uchida | | 2007/0260117 A1 | 11/2007 | Zwolinski et al. |
| 2006/0281970 A1 | 12/2006 | Stokes et al. | | 2007/0260121 A1 | 11/2007 | Bakos et al. |
| 2006/0282106 A1 | 12/2006 | Cole et al. | | 2007/0260242 A1 | 11/2007 | Dycus et al. |
| 2006/0285732 A1 | 12/2006 | Horn et al. | | 2007/0260273 A1 | 11/2007 | Cropper et al. |
| 2006/0287644 A1 | 12/2006 | Inganas et al. | | 2007/0270629 A1 | 11/2007 | Charles |
| 2006/0287666 A1 | 12/2006 | Saadat et al. | | 2007/0270889 A1 | 11/2007 | Conlon et al. |
| 2006/0293626 A1 | 12/2006 | Byrum et al. | | 2007/0270895 A1 | 11/2007 | Nobis et al. |
| 2007/0002135 A1 | 1/2007 | Glukhovsky | | 2007/0270907 A1 | 11/2007 | Stokes et al. |
| 2007/0005019 A1 | 1/2007 | Okishige | | 2007/0282165 A1 | 12/2007 | Hopkins et al. |

| | | | | | | |
|---|---|---|---|---|---|---|
| 2007/0282371 A1 | 12/2007 | Lee et al. | | 2009/0125042 A1 | 5/2009 | Mouw |
| 2007/0293727 A1 | 12/2007 | Goldfarb et al. | | 2009/0131751 A1 | 5/2009 | Spivey et al. |
| 2007/0299387 A1 | 12/2007 | Williams et al. | | 2009/0131932 A1 | 5/2009 | Vakharia et al. |
| 2008/0004650 A1 | 1/2008 | George | | 2009/0131933 A1 | 5/2009 | Ghabrial et al. |
| 2008/0015409 A1 | 1/2008 | Barlow et al. | | 2009/0143639 A1 | 6/2009 | Stark |
| 2008/0015413 A1 | 1/2008 | Barlow et al. | | 2009/0143649 A1 | 6/2009 | Rossi |
| 2008/0015552 A1 | 1/2008 | Doyle et al. | | 2009/0143794 A1 | 6/2009 | Conlon et al. |
| 2008/0021416 A1 | 1/2008 | Arai et al. | | 2009/0143818 A1 | 6/2009 | Faller et al. |
| 2008/0022927 A1 | 1/2008 | Zhang et al. | | 2009/0149710 A1 | 6/2009 | Stefanchik et al. |
| 2008/0027387 A1 | 1/2008 | Grabinsky | | 2009/0177031 A1 | 7/2009 | Surti et al. |
| 2008/0033451 A1 | 2/2008 | Rieber et al. | | 2009/0177219 A1 | 7/2009 | Conlon |
| 2008/0051629 A1 | 2/2008 | Sugiyama et al. | | 2009/0182332 A1 | 7/2009 | Long et al. |
| 2008/0051735 A1 | 2/2008 | Measamer et al. | | 2009/0192344 A1 | 7/2009 | Bakos et al. |
| 2008/0058586 A1 | 3/2008 | Karpiel | | 2009/0192534 A1 | 7/2009 | Ortiz et al. |
| 2008/0058854 A1 | 3/2008 | Kieturakis et al. | | 2009/0198231 A1 | 8/2009 | Esser et al. |
| 2008/0065169 A1 | 3/2008 | Colliou et al. | | 2009/0198253 A1 | 8/2009 | Omori |
| 2008/0071264 A1 | 3/2008 | Azure | | 2009/0210000 A1 | 8/2009 | Sullivan et al. |
| 2008/0086172 A1 | 4/2008 | Martin et al. | | 2009/0216248 A1 | 8/2009 | Uenohara et al. |
| 2008/0097159 A1 | 4/2008 | Ishiguro | | 2009/0227828 A1 | 9/2009 | Swain et al. |
| 2008/0097472 A1 | 4/2008 | Agmon et al. | | 2009/0248055 A1 | 10/2009 | Spivey et al. |
| 2008/0097483 A1 | 4/2008 | Ortiz et al. | | 2009/0269317 A1 | 10/2009 | Davalos |
| 2008/0103527 A1 | 5/2008 | Martin et al. | | 2009/0281559 A1 | 11/2009 | Swain et al. |
| 2008/0114384 A1 | 5/2008 | Chang et al. | | 2009/0287206 A1 | 11/2009 | Jun |
| 2008/0119870 A1 | 5/2008 | Williams | | 2009/0287236 A1 | 11/2009 | Bakos et al. |
| 2008/0119891 A1 | 5/2008 | Miles et al. | | 2009/0292164 A1 | 11/2009 | Yamatani |
| 2008/0125796 A1 | 5/2008 | Graham | | 2009/0299135 A1 | 12/2009 | Spivey |
| 2008/0132892 A1 | 6/2008 | Lunsford et al. | | 2009/0299143 A1 | 12/2009 | Conlon et al. |
| 2008/0139882 A1 | 6/2008 | Fujimori | | 2009/0299362 A1 | 12/2009 | Long et al. |
| 2008/0140069 A1 | 6/2008 | Filloux et al. | | 2009/0299385 A1 | 12/2009 | Stefanchik et al. |
| 2008/0140071 A1 | 6/2008 | Vegesna | | 2009/0299406 A1 | 12/2009 | Swain et al. |
| 2008/0147113 A1 | 6/2008 | Nobis et al. | | 2009/0299409 A1 | 12/2009 | Coe et al. |
| 2008/0171907 A1 | 7/2008 | Long et al. | | 2009/0306658 A1 | 12/2009 | Nobis et al. |
| 2008/0177135 A1 | 7/2008 | Muyari et al. | | 2009/0306683 A1 | 12/2009 | Zwolinski et al. |
| 2008/0188710 A1 | 8/2008 | Segawa et al. | | 2009/0322864 A1 | 12/2009 | Karasawa et al. |
| 2008/0188868 A1 | 8/2008 | Weitzner et al. | | 2009/0326332 A1 | 12/2009 | Carter |
| 2008/0200755 A1 | 8/2008 | Bakos | | 2009/0326561 A1 | 12/2009 | Carroll, II et al. |
| 2008/0200762 A1 | 8/2008 | Stokes et al. | | 2010/0010294 A1 | 1/2010 | Conlon et al. |
| 2008/0200911 A1 | 8/2008 | Long | | 2010/0010298 A1 | 1/2010 | Bakos et al. |
| 2008/0200933 A1 | 8/2008 | Bakos et al. | | 2010/0010299 A1 | 1/2010 | Bakos et al. |
| 2008/0200934 A1 | 8/2008 | Fox | | 2010/0010303 A1 | 1/2010 | Bakos |
| 2008/0208213 A1 | 8/2008 | Benjamin et al. | | 2010/0010510 A1 | 1/2010 | Stefanchik |
| 2008/0221587 A1 | 9/2008 | Schwartz | | 2010/0010511 A1 | 1/2010 | Harris et al. |
| 2008/0228213 A1 | 9/2008 | Blakeney et al. | | 2010/0023032 A1 | 1/2010 | Granja Filho |
| 2008/0230972 A1 | 9/2008 | Ganley | | 2010/0030211 A1 | 2/2010 | Davalos et al. |
| 2008/0234696 A1 | 9/2008 | Taylor et al. | | 2010/0036198 A1 | 2/2010 | Tacchino et al. |
| 2008/0243106 A1 | 10/2008 | Coe et al. | | 2010/0042045 A1 | 2/2010 | Splvey |
| 2008/0243148 A1 | 10/2008 | Mikkaichi et al. | | 2010/0048990 A1 | 2/2010 | Bakos |
| 2008/0243176 A1 | 10/2008 | Weitzner et al. | | 2010/0049190 A1 | 2/2010 | Long et al. |
| 2008/0249567 A1 | 10/2008 | Kaplan | | 2010/0049223 A1 | 2/2010 | Granja Filho |
| 2008/0262513 A1 | 10/2008 | Stahler et al. | | 2010/0056861 A1 | 3/2010 | Spivey |
| 2008/0262540 A1 | 10/2008 | Bangera et al. | | 2010/0056862 A1 | 3/2010 | Bakos |
| 2008/0269782 A1 | 10/2008 | Stefanchik et al. | | 2010/0056864 A1 | 3/2010 | Lee |
| 2008/0269783 A1 | 10/2008 | Griffith | | 2010/0057085 A1 | 3/2010 | Holcomb et al. |
| 2008/0275474 A1 | 11/2008 | Martin et al. | | 2010/0057108 A1 | 3/2010 | Spivey et al. |
| 2008/0275475 A1 | 11/2008 | Schwemberger et al. | | 2010/0063538 A1 | 3/2010 | Spivey et al. |
| 2008/0287737 A1 | 11/2008 | Dejima | | 2010/0076451 A1 | 3/2010 | Zwolinski et al. |
| 2008/0287983 A1 | 11/2008 | Smith et al. | | 2010/0081877 A1 | 4/2010 | Vakharia |
| 2008/0300461 A1 | 12/2008 | Shaw et al. | | 2010/0087813 A1 | 4/2010 | Long |
| 2008/0300547 A1 | 12/2008 | Bakos | | 2010/0091128 A1 | 4/2010 | Ogasawara et al. |
| 2008/0309758 A1 | 12/2008 | Karasawa et al. | | 2010/0113872 A1 | 5/2010 | Asada et al. |
| 2008/0312496 A1 | 12/2008 | Zwolinski | | 2010/0121362 A1 | 5/2010 | Clague et al. |
| 2008/0312499 A1 | 12/2008 | Handa et al. | | 2010/0130817 A1 | 5/2010 | Conlon |
| 2008/0312500 A1 | 12/2008 | Asada et al. | | 2010/0130975 A1 | 5/2010 | Long |
| 2008/0312506 A1 | 12/2008 | Spivey et al. | | 2010/0131005 A1 | 5/2010 | Conlon |
| 2008/0319436 A1 | 12/2008 | Daniel et al. | | 2010/0152539 A1 | 6/2010 | Ghabrial et al. |
| 2008/0319439 A1 | 12/2008 | Ootsubu | | 2010/0152609 A1 | 6/2010 | Zwolinski et al. |
| 2009/0005636 A1 | 1/2009 | Pang et al. | | 2010/0152746 A1 | 6/2010 | Ceniccola et al. |
| 2009/0054728 A1 | 2/2009 | Trusty | | 2010/0179510 A1 | 7/2010 | Fox et al. |
| 2009/0062788 A1 | 3/2009 | Long et al. | | 2010/0179530 A1 | 7/2010 | Long et al. |
| 2009/0062792 A1 | 3/2009 | Vakharia et al. | | 2010/0191050 A1 | 7/2010 | Zwolinski |
| 2009/0062795 A1 | 3/2009 | Vakharia et al. | | 2010/0191267 A1 | 7/2010 | Fox |
| 2009/0069634 A1 | 3/2009 | Larkin | | 2010/0198005 A1 | 8/2010 | Fox |
| 2009/0076499 A1 | 3/2009 | Azure | | 2010/0198149 A1 | 8/2010 | Fox |
| 2009/0078736 A1 | 3/2009 | Van Lue | | 2010/0198244 A1 | 8/2010 | Spivey et al. |
| 2009/0082776 A1 | 3/2009 | Cresina | | 2010/0198248 A1 | 8/2010 | Vakharia |
| 2009/0082779 A1 | 3/2009 | Nakao | | 2010/0217367 A1 | 8/2010 | Belson |
| 2009/0112059 A1 | 4/2009 | Nobis | | 2010/0249700 A1 | 9/2010 | Spivey |
| 2009/0112062 A1 | 4/2009 | Bakos | | 2010/0261994 A1 | 10/2010 | Davalos et al. |
| 2009/0112063 A1 * | 4/2009 | Bakos et al. ............ 600/114 | | 2010/0286791 A1 | 11/2010 | Goldsmith |

| | | | | | | |
|---|---|---|---|---|---|---|
| 2010/0298642 | A1 | 11/2010 | Trusty et al. | EP | 1836980 A1 | 9/2007 |
| 2010/0312056 | A1 | 12/2010 | Galperin et al. | EP | 1854421 A2 | 11/2007 |
| 2010/0331622 | A2 | 12/2010 | Conlon | EP | 1857061 A1 | 11/2007 |
| 2010/0331758 | A1 | 12/2010 | Davalos et al. | EP | 1875876 A1 | 1/2008 |
| 2010/0331774 | A2 | 12/2010 | Spivey | EP | 1891881 A1 | 2/2008 |
| 2011/0077476 | A1 | 3/2011 | Rofougaran | EP | 1902663 A1 | 3/2008 |
| 2011/0093009 | A1 | 4/2011 | Fox | EP | 1477106 B1 | 6/2008 |
| 2011/0098694 | A1 | 4/2011 | Long | EP | 1949844 A1 | 7/2008 |
| 2011/0098704 | A1 | 4/2011 | Long et al. | EP | 1518499 B1 | 8/2008 |
| 2011/0105850 | A1 | 5/2011 | Voegele et al. | EP | 1582138 B1 | 9/2008 |
| 2011/0106221 | A1 | 5/2011 | Neal, II et al. | EP | 1709918 B1 | 10/2008 |
| 2011/0112434 | A1 | 5/2011 | Ghabrial et al. | EP | 1985226 A2 | 10/2008 |
| 2011/0115891 | A1 | 5/2011 | Trusty | EP | 1994904 A1 | 11/2008 |
| 2011/0124964 | A1 | 5/2011 | Nobis | EP | 1707130 B1 | 12/2008 |
| 2011/0152609 | A1 | 6/2011 | Trusty et al. | EP | 0723462 B1 | 3/2009 |
| 2011/0152610 | A1 | 6/2011 | Trusty et al. | EP | 1769749 B1 | 11/2009 |
| 2011/0152858 | A1 | 6/2011 | Long et al. | EP | 1493397 B1 | 9/2011 |
| 2011/0152859 | A1 | 6/2011 | Long et al. | FR | 2731610 A1 | 9/1996 |
| 2011/0152878 | A1 | 6/2011 | Trusty et al. | GB | 330629 A | 6/1930 |
| 2011/0152923 | A1 | 6/2011 | Fox | GB | 2335860 A | 10/1999 |
| 2011/0160514 | A1 | 6/2011 | Long et al. | GB | 2403909 A | 1/2005 |
| 2011/0190659 | A1 | 8/2011 | Long et al. | GB | 2421190 A | 6/2006 |
| 2011/0190764 | A1 | 8/2011 | Long et al. | GB | 2443261 A | 4/2008 |
| 2011/0193948 | A1 | 8/2011 | Amling et al. | JP | 56-46674 | 4/1981 |
| 2011/0245619 | A1 | 10/2011 | Holcomb | JP | 63309252 A | 12/1988 |
| 2011/0285488 | A1 | 11/2011 | Scott et al. | JP | 4038960 A | 2/1992 |
| 2011/0306971 | A1 | 12/2011 | Long | JP | 8-29699 A | 2/1996 |
| 2012/0004502 | A1 | 1/2012 | Weitzner et al. | JP | 2000245683 A | 9/2000 |
| 2012/0088965 | A1 | 4/2012 | Stokes et al. | JP | 2002-369791 A | 12/2002 |
| 2012/0089089 | A1 | 4/2012 | Swain et al. | JP | 2003-088494 A | 3/2003 |
| 2012/0089093 | A1 | 4/2012 | Trusty | JP | 2003-235852 A | 8/2003 |
| 2012/0116155 | A1 | 5/2012 | Trusty | JP | 2004-33525 A | 2/2004 |
| 2012/0179148 | A1 | 7/2012 | Conlon | JP | 2004-065745 A | 3/2004 |
| 2012/0191075 | A1 | 7/2012 | Trusty | JP | 2005-121947 A | 5/2005 |
| 2012/0191076 | A1 | 7/2012 | Voegele et al. | JP | 2005-261514 A | 9/2005 |
| 2012/0220998 | A1 | 8/2012 | Long et al. | JP | 2006297005 A | 11/2006 |
| 2012/0220999 | A1 | 8/2012 | Long | JP | 2006343510 A * | 12/2006 |
| 2012/0221002 | A1 | 8/2012 | Long et al. | NL | 1021295 C2 | 2/2004 |
| 2012/0238796 | A1 | 9/2012 | Conlon | SU | 194230 | 5/1967 |
| | | | | SU | 980703 | 12/1982 |
| FOREIGN PATENT DOCUMENTS | | | | WO | WO 84/01707 A1 | 5/1984 |
| DE | 4323585 A1 | 1/1995 | | WO | WO 92/13494 A1 | 8/1992 |
| DE | 19713797 A1 | 10/1997 | | WO | WO 93/10850 A1 | 6/1993 |
| DE | 19757056 B4 | 8/2008 | | WO | WO 93/20760 A1 | 10/1993 |
| DE | 102006027873 B4 | 10/2009 | | WO | WO 93/20765 A1 | 10/1993 |
| EP | 0086338 A1 | 8/1983 | | WO | WO 95/09666 A1 | 4/1995 |
| EP | 0286415 A2 | 10/1988 | | WO | WO 96/22056 A1 | 7/1996 |
| EP | 0589454 A2 | 3/1994 | | WO | WO 96/27331 A1 | 9/1996 |
| EP | 0464479 B1 | 3/1995 | | WO | WO 96/39946 A1 | 12/1996 |
| EP | 0529675 B1 | 2/1996 | | WO | WO 97/12557 A1 | 4/1997 |
| EP | 0621009 B1 | 7/1997 | | WO | WO 98/01080 A1 | 1/1998 |
| EP | 0724863 B1 | 7/1999 | | WO | WO 99/00060 A1 | 1/1999 |
| EP | 0760629 B1 | 11/1999 | | WO | WO 99/09919 A1 | 3/1999 |
| EP | 0818974 B1 | 7/2001 | | WO | WO 99/17661 A1 | 4/1999 |
| EP | 1281356 A2 | 2/2003 | | WO | WO 99/30622 A2 | 6/1999 |
| EP | 0947166 B1 | 5/2003 | | WO | WO 00/35358 A1 | 6/2000 |
| EP | 0836832 B1 | 12/2003 | | WO | WO 01/10319 A1 | 2/2001 |
| EP | 1402837 A1 | 3/2004 | | WO | WO 01/26708 A1 | 4/2001 |
| EP | 0744918 B1 | 4/2004 | | WO | WO 01/41627 A2 | 6/2001 |
| EP | 0931515 B1 | 8/2004 | | WO | WO 01/58360 A2 | 8/2001 |
| EP | 0941128 B1 | 10/2004 | | WO | WO 02/11621 A1 | 2/2002 |
| EP | 1411843 B1 | 10/2004 | | WO | WO 02/34122 A2 | 5/2002 |
| EP | 1150614 B1 | 11/2004 | | WO | WO 02/094082 A2 | 11/2002 |
| EP | 1477104 A1 | 11/2004 | | WO | WO 03/045260 A1 | 6/2003 |
| EP | 1481642 A1 | 12/2004 | | WO | WO 03/047684 A2 | 6/2003 |
| EP | 1493391 A1 | 1/2005 | | WO | WO 03/059412 A2 | 7/2003 |
| EP | 0848598 B1 | 2/2005 | | WO | WO 03/078721 A2 | 9/2003 |
| EP | 1281360 B1 | 3/2005 | | WO | WO 03/081761 A2 | 10/2003 |
| EP | 1568330 A1 | 8/2005 | | WO | WO 03/082129 A2 | 10/2003 |
| EP | 1452143 B1 | 9/2005 | | WO | WO 2004/006789 A1 | 1/2004 |
| EP | 1616527 A2 | 1/2006 | | WO | WO 2004/028613 A2 | 4/2004 |
| EP | 1006888 B1 | 3/2006 | | WO | WO 2004/037123 A1 | 5/2004 |
| EP | 1629764 A1 | 3/2006 | | WO | WO 2004/037149 A1 | 5/2004 |
| EP | 1013229 B1 | 6/2006 | | WO | WO 2004/052221 A1 | 6/2004 |
| EP | 1721561 A1 | 11/2006 | | WO | WO 2004/086984 A1 | 10/2004 |
| EP | 1153578 B1 | 3/2007 | | WO | WO 2005/009211 A2 | 2/2005 |
| EP | 1334696 B1 | 3/2007 | | WO | WO 2005/018467 A2 | 3/2005 |
| EP | 1769766 A1 | 4/2007 | | WO | WO 2005/037088 A2 | 4/2005 |
| EP | 1836971 A2 | 9/2007 | | WO | WO 2005/048827 A1 | 6/2005 |

| | | |
|---|---|---|
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Feb. 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastomosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/ Approximation Device; [online] URL: http://www.usgimedical. com/eos/components-gprox.htm—accessed May 30, 2008 (2 pages).
Printout of web page—http://www.vacumed.com/zcom/product/ Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http:// www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).

Hakko Retractors, obtained Aug. 25, 2009 (5 pages).

Zadno et al., "Linear Superelasticity in Cold-Worked NI-TI," Engineering Aspects of Shape Memory Alloys, pp. 414-419.

U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.

International Preliminary Report on Patentability for PCT/US2010/060242, Jun. 19, 2012 (8 pages).

Zadno et al., "Linear Superelasticity in Cold-Worked NI-TI," Engineering Aspects of Shape Memory Alloys, pp. 414-419 (1990).

How Stuff Works "How Smart Structures Will Work," http://science.howstuffworks.com/engineering/structural/smart-structure1.htm; accessed online Nov. 1, 2011 (3 pages).

Instant Armor: Science Videos—Science News—ScienCentral; http://www.sciencentral.com/articlesiview.php3?article_id=218392121; accessed online Nov. 1, 2011 (2 pages).

Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).

Jolly et al., Properties and Applications of Commercial Magnetorheological Fluids. SPIE 5th Annual Int. Symposium on Smart Structures and Materials, 1998 (18 pages).

Rutala et al. "Guideline for Disinfection and Sterilization in Healthcare Facilities, 2008" (available at http://www.cdc.gov/hicpac/Disinfection_Sterilization/13_11sterilizingPractices.html).

U.S. Appl. No. 13/267,251, filed Oct. 6, 2011.
U.S. Appl. No. 13/325,791, filed Dec. 14, 2011.
U.S. Appl. No. 13/399,358, filed Feb. 17, 2012.
U.S. Appl. No. 13/420,818, filed Mar. 15, 2012.

* cited by examiner

SELECTIVELY POSITIONABLE CAMERA FOR SURGICAL GUIDE TUBE ASSEMBLY

BACKGROUND

The embodiments relate, in general, to endoscopes and medical procedures and, more particularly, to devices for facilitating the insertion and manipulation of endoscopic guide tube assemblies and other surgical instruments within a body cavity to accomplish various surgical and therapeutic procedures.

Minimally invasive procedures are desirable because such procedures can reduce pain and provide relatively quick recovery times as compared with conventional open medical procedures. Many minimally invasive procedures are performed through one or more ports through the abdominal wall, commonly known as trocars. A laparascope that may or may not include a camera may be used through one of these ports for visualization of the anatomy and surgical instruments may be used simultaneously through other ports. Such devices and procedures permit a physician to position, manipulate, and view anatomy, surgical instruments and accessories inside the patient through a small access opening in the patient's body.

Still less invasive procedures include those that are performed through insertion of an endoscope through a natural body orifice to a treatment region. Examples of this approach include, but are not limited to, cystoscopy, hysteroscopy, esophagogastroduodenoscopy, and colonoscopy. Many of these procedures employ the use of a flexible endoscope and flexible or steerable guide tube assemblies during the procedure. Flexible endoscopes often have a flexible, steerable articulating section near the distal end that can be controlled by the user utilizing controls at the proximal end. Treatment or diagnosis may be completed intralumenally, such as polypectomy or gastroscopy. Alternatively, treatment or diagnosis of extra-luminal anatomy in the abdominal cavity may be completed translumenally, for example, through a gastrotomy, colonotomy or vaginotomy. Minimally invasive therapeutic procedures to treat or diagnose diseased tissue by introducing medical instruments translumenally to a tissue treatment region through a natural opening of the patient are known as Natural Orifice Translumenal Endoscopic Surgery (NOTES™).

Regardless of the type of surgery involved and the method in which the endoscope is inserted into the body, the clinicians and surgical specialists performing such procedures have generally developed skill sets and approaches that rely on anatomical alignment for both visualization and tissue manipulation purposes. Over the years, a variety of different endoscope arrangements, as well as various types of steerable sheaths, guide tubes and overtubes for accommodating endoscopes have been developed. For example, various endoscopic guide systems and endoscopes are disclosed in U.S. patent application Ser. No. 12/468,462, entitled "Manipulatable Guide System and Methods For Natural Orifice Translumenal Endoscopic Surgery", filed May 19, 2009, the disclosure of which is herein incorporated by reference in its entirety. Some of the guide system embodiments disclosed therein include extended articulatable working channels as well as a liftable camera device. Such configurations afford the clinician with the ability to advantageously manipulate and position the working channels while providing the flexibility to position the camera to provide a "bird's eye", "stadium", or laparoscopic view of the theater.

While these and other overtube systems and endoscopic surgical devices represent great advancements in the field of Natural Orifice Translumenal Endoscopic Surgery, various surgical procedures require the simultaneous use and manipulation of several of such devices. For example, typical NOTES procedures being done today employ a standard gastroscope through an overtube to gain access and conduct the surgical procedure through the working channels in the gastroscope. The clinician commonly uses one hand to manage the overtube and the second hand to rotate and/or articulate the gastroscope. Other operations might require the use of three or more surgical instruments, making their coordination and precise manipulation challenging. Similarly some overtube arrangements that can articulate in four directions require the clinician to use both hands to operate. Such manipulation is also complicated due to the need for the clinician to also position and manipulate a camera.

Consequently a need exists for a selectively positionable camera assembly for use with guide tube assemblies employed to guide and support a plurality of endoscopic surgical devices.

The foregoing discussion is intended only to illustrate some of the shortcomings present in the field at the time, and should not be taken as a disavowal of claim scope.

SUMMARY

In connection with one general aspect of the present invention there is provided a selectively positionable camera assembly for use in connection with a guide tube assembly that having a guide tube handle portion and at least one guide tube therein. In various embodiments, the camera assembly comprises an elongated flexible camera portion that is sized to operably extend through one of the at least one guide tubes of the guide tube assembly. A camera handle may be operably coupled to the elongated flexible camera portion. The camera handle is movably supported by at least a portion of the guide tube handle portion. A retainer is provided on one of the camera handle or the portion of the guide tube handle for releasably retaining the camera handle in any one of a plurality of orientations relative to the portion of said guide tube handle.

In connection with yet another general aspect of the present invention there is provided a selectively positionable camera assembly for use in connection with a guide tube assembly that has a guide tube handle portion and at least one guide tube therein. In various embodiments, the camera assembly comprises an elongated flexible camera portion that is sized to operably extend through one of the at least one guide tubes of the guide tube assembly. A camera handle may be operably coupled to the elongated flexible camera portion. The camera handle is movably supported by at least a portion of the guide tube handle portion. Means for selectively retaining the camera handle in any one of a plurality of orientations relative to the portion of said guide tube handle are provided.

In connection with another general aspect of the present invention there is provided a camera kit for use with a guide tube assembly having a guide tube handle portion and at least one hollow guide tube therein. The camera kit may comprise a camera interface adapter that is coupleable to the guide tube handle portion. The camera interface adapter may have a hollow passage that extends through the adapter. The camera kit may further include a camera that has an elongated flexible camera portion that is sized to operably extend through the hollow passage in the camera interface adapter and one of the at least one guide tubes of the guide tube assembly. A camera handle may be operably coupled to the elongated flexible camera portion. The camera handle may have a distal portion that is sized to be movably supported within the hollow passage in the camera interface adapter. A retainer may be provided on at least one of the camera interface adapter and camera handle for releasably retaining the distal portion of the camera handle in any one of a plurality of orientations within the passage in the camera interface adapter.

BRIEF DESCRIPTION OF THE FIGURES

The novel features of the embodiments described herein are set forth with particularity in the appended claims. The embodiments, however, both as to organization and methods of operation may be better understood by reference to the following description, taken in conjunction with the accompanying drawings as follows.

DETAILED DESCRIPTION

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Such modifications and variations are intended to be included within the scope of the appended claims.

Figure 1:
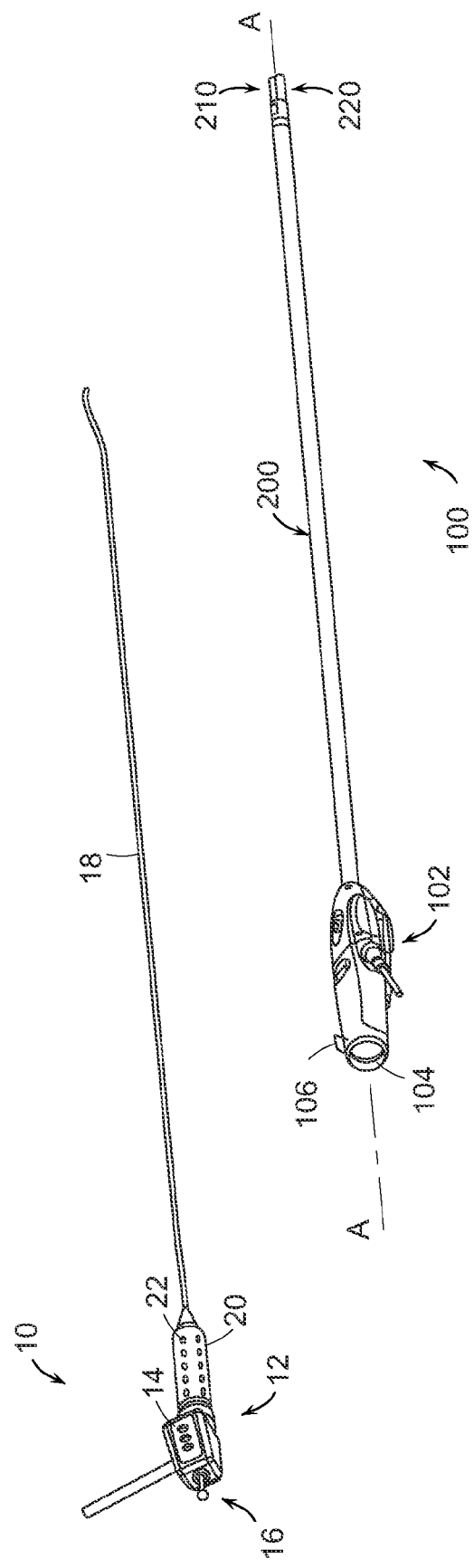
FIG. 1 is an exploded view of a camera and guide tube assembly embodiment of the present invention.

The various embodiments generally relate to cameras used in connection with guide systems and steerable sheath arrangements for use in connection with endoscopes for selectively positioning and manipulating endoscopic tools in a desired orientation within the body cavity. FIG. 1 illustrates a flexible endoscopic camera 10 that may be advantageously employed in connection with a steerable guide tube assembly 100. Various steerable guide tube assemblies are known and, as such, the various details of the steerable guide tube assembly 100 will not be described herein beyond what is necessary to understand the various embodiments of the present invention. For example, the steerable guide tube assembly 100 may include a flexible insertion tube 200 that operably supports two or more steerable working channels 210, 220.

Figure 2:
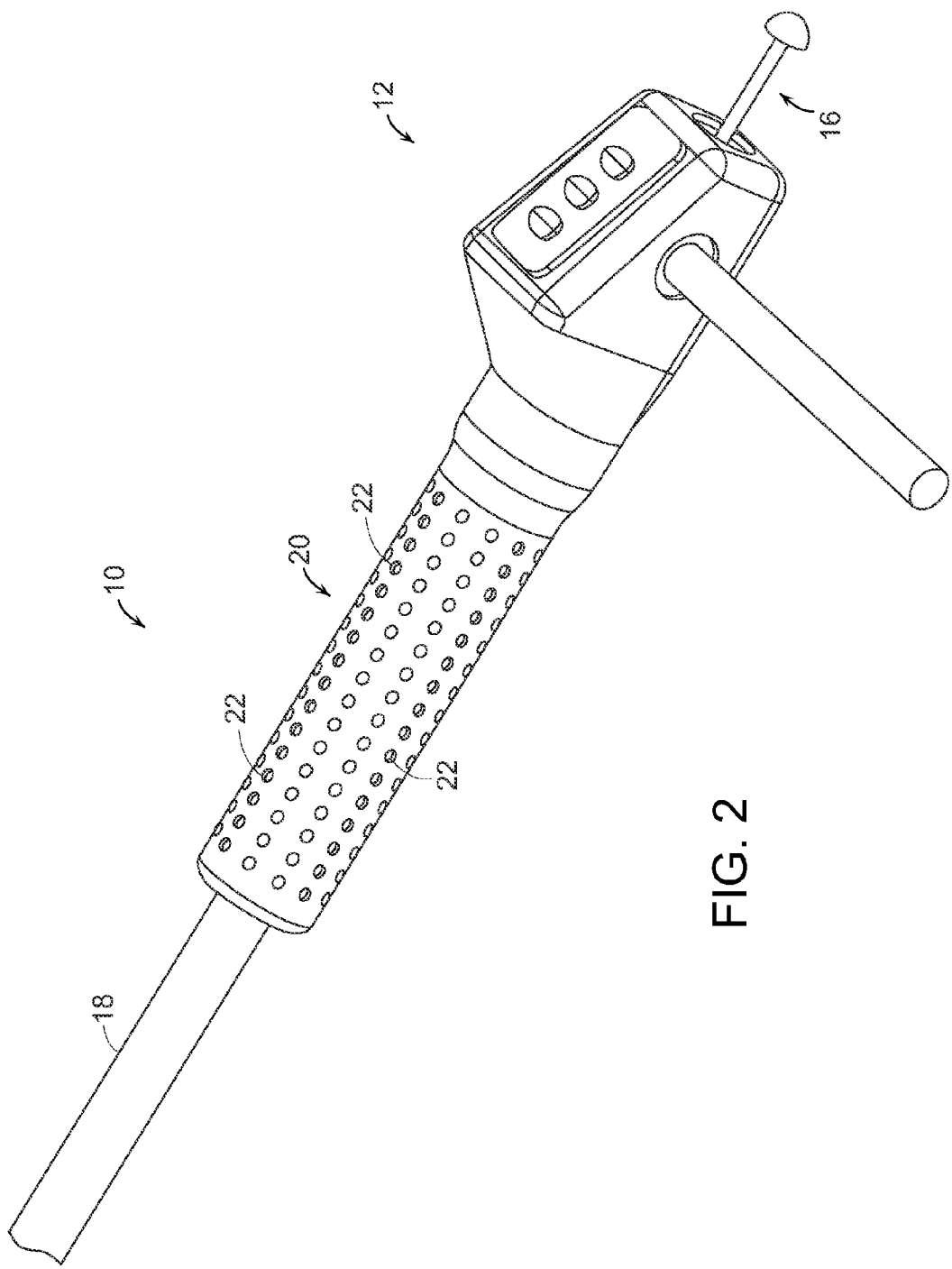
FIG. 2 is a partial perspective view of a camera embodiment of the present invention.

In various embodiments, the camera 10 may include a handle portion 12 that supports a series of control buttons 14 and a joy stick arrangement 16 for selectively steering the flexible portion 18. See FIGS. 1 and 2. In various embodiments, the handle portion 12 includes a distal barrel portion 20 that may be provided with a series of dimples 22 therein. The distal barrel portion 20 is sized to be slidably inserted into a passage 104 in the proximal handle portion 102 of the steerable guide tube assembly 100. To retain the camera 10 in the desired position, the proximal handle portion 102 may be provided with at least one spring-biased ball detent assembly 106 that will retainingly engage a dimple 1912 in registration therewith. Thus, the clinician can adjust the position of the camera 10 axially along axis A-A as well as rotationally about axis A-A.

Figure 3:
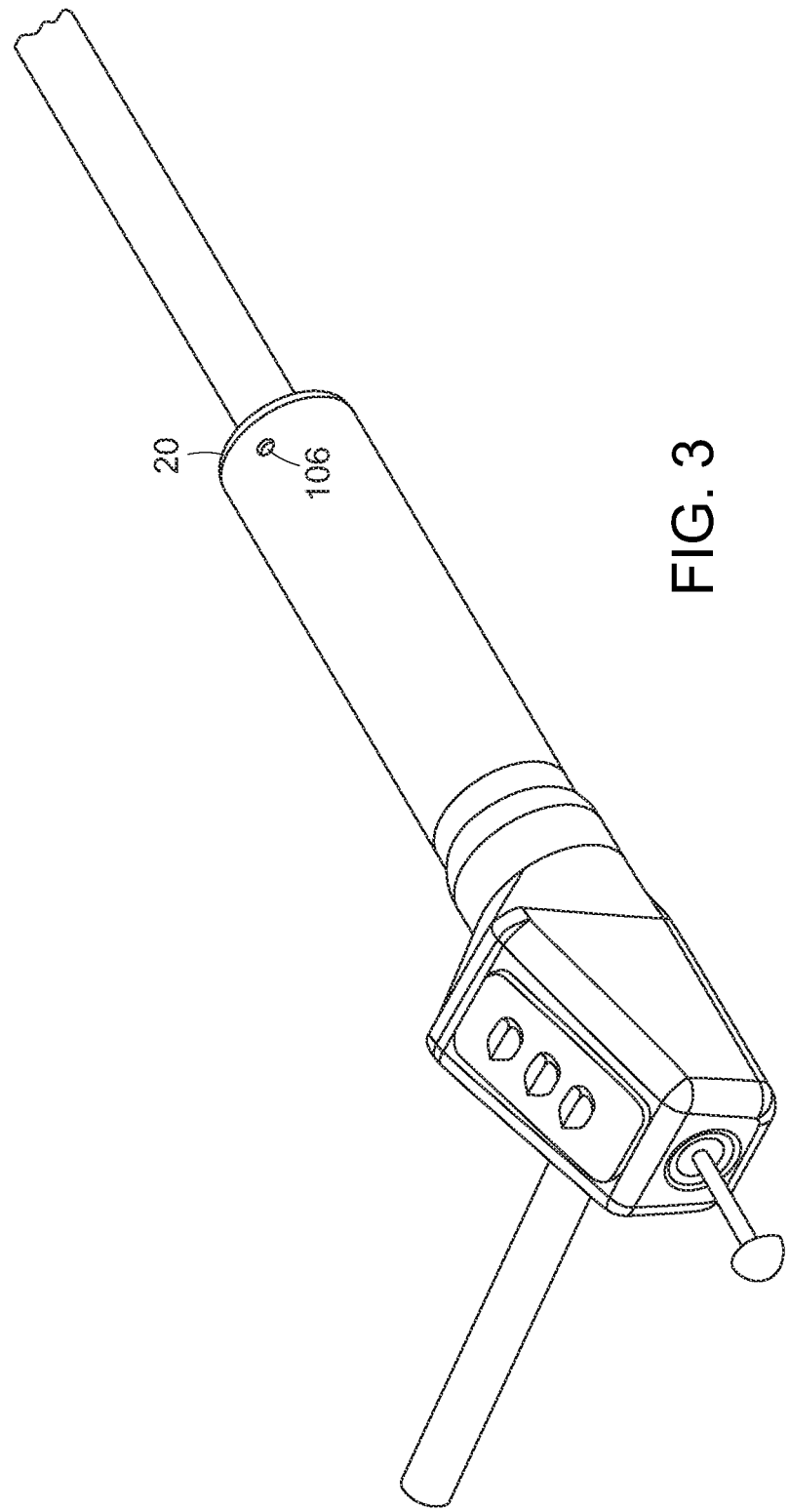
FIG. 3 is a partial perspective view of another camera embodiment of the present invention.
Figure 4:
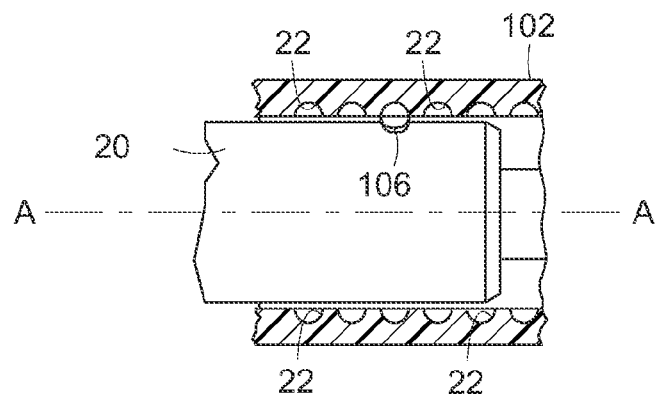
FIG. 4 is a partial cross-section view of a portion of a camera inserted into the handle portion of a guide tube assembly of another embodiment of the present invention.
Figure 6:
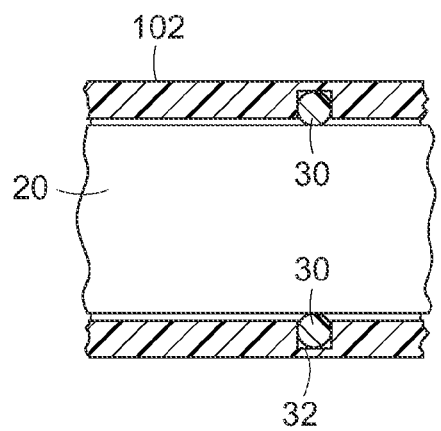
FIG. 6 is a partial cross-section view of a portion of a camera inserted into the handle portion of a guide tube assembly of another embodiment of the present invention.
Figure 7:
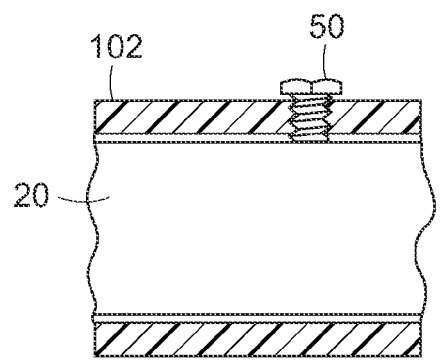
FIG. 7 is a partial cross-section view of a portion of a camera inserted into the handle portion of a guide tube assembly of another embodiment of the present invention.
Figure 5:
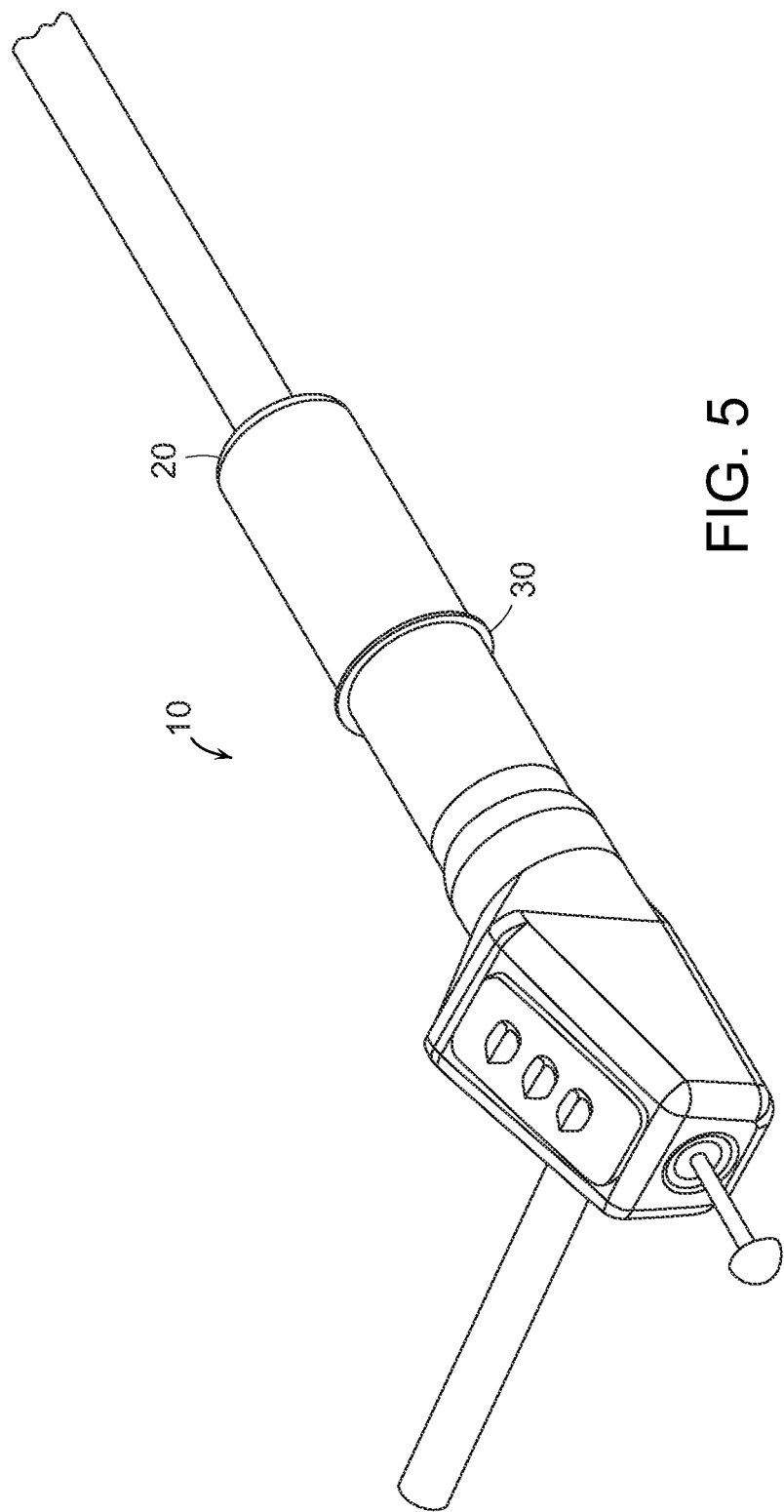
FIG. 5 is a partial perspective view of another camera embodiment of the present invention.

In alternative embodiments, the series of dimples 22 may be provided on the inner wall of the passage 104 and one or more spring biased ball detents 106 may be provided on the distal barrel portion 1910. See FIGS. 3 and 4. In still other embodiments, one or more O-rings 30 may be provided on the distal barrel portion 20 of the camera 10 to enable the camera 10 to be moved axially along axis A-A and rotatably about axis A-A within the passage 104, yet retain the camera 10 in position after it has been manipulated therein. See FIG. 5. In another embodiment, one or more O-rings 30 may be journaled within grooves 32 in the handle portion 102. See FIG. 6. In still other embodiments, one or more set screws 50 may be provided through handle 102 to selectively lock the camera 10 in a desired position within the handle passage 104. See FIG. 7.

Figure 8:
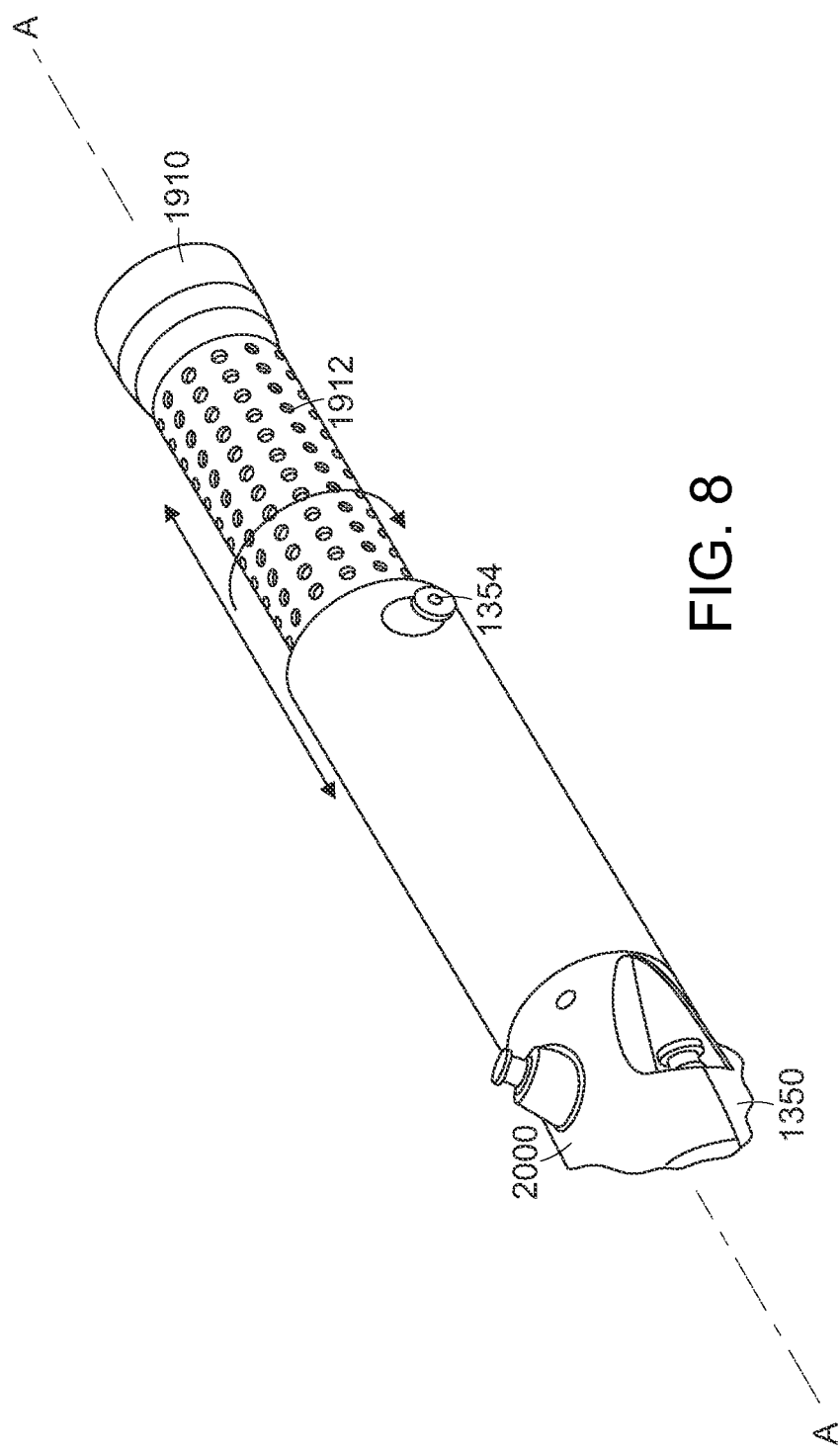
FIG. 8 is a partial perspective view of a camera and adapter tube arrangement of another embodiment of the present invention.

In other embodiments, the proximal handle portion 102 may be provided without the spring biased ball detent and be interchangeable with a handle adapter tube 60 that can be removably attached to the distal handle segment 102 of the steerable guide tube assembly 100 by snap features, screws, etc. In those embodiments, the handle adapter tube 60 is provided with at least one spring-biased spring detent 106 or the series of dimples 22, depending upon the camera handle configuration. See FIG. 8.

Those of ordinary skill in the art will appreciate that the above-described camera mounting configuration provides a unique and novel user interface for adjustably locking the handle of the flexible endoscopic camera to the handle portion of a steerable guide tube assembly. It will be further appreciated, however, that such camera interface configuration may also be successfully employed in connection with other types and forms of channel access platforms without departing from the spirit and scope of the present invention. Such interface may be designed so that it facilitates the loading of the endoscopic camera into the access platform camera channel and then locks onto the access platform handle so that the two handles merge into one handle for the purpose of manipulation. The interface provides a means for easy adjustment in two axes. The endoscopic camera can slide in and out along the axis of the camera catheter to adjust how much the camera tip is exposed at the distal end of the access platform. The endoscopic camera can also be rotationally adjusted in order to maintain the desired view orientation at the surgical site. Such arrangement permits the clinician to place anatomical references in a comfortable viewing orientation regardless of the access platform orientation.

While the embodiments have been described, it should be apparent, however, that various modifications, alterations and adaptations to the embodiments may occur to persons skilled in the art with the attainment of some or all of the advantages of the invention. For example, according to various embodiments, a single component may be replaced by multiple components, and multiple components may be replaced by a single component, to perform a given function or functions.

This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include a combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A selectively positionable camera assembly for use in connection with a guide tube assembly having a guide tube handle portion and at least one guide tube therein, said camera assembly comprising:
    an elongated flexible camera portion sized to operably extend through one of the at least one guide tubes of the guide tube assembly;
    a camera handle operably coupled to said elongated flexible camera portion and being movably supported by at least a portion of the guide tube handle portion; and
    a retainer on at least one of said portion of said guide tube handle and said camera handle for releasably retaining said camera handle in a first orientation and in a second orientation relative to said portion of said guide tube handle, wherein said camera handle is released from said first orientation, transitioned to said second orientation, and retained in said second orientation by moving at least one of said camera handle and said portion of said guide tube handle relative to said other one of said camera handle and said portion of said guide tube handle.

2. The camera assembly of claim 1 wherein said camera handle comprises a distal barrel portion that has a series of dimples formed therein, said distal barrel portion being sized to be movably received within a passage in said guide tube handle portion and wherein said retainer comprises at least one spring biased ball detent in said guide tube handle portion for retaining engagement with anyone of said series of dimples.

3. The camera assembly of claim 1 wherein said camera handle comprises a distal barrel portion that is sized to be movably received within a passage in said guide tube handle portion and wherein said retainer comprises at least one spring biased ball detent in said distal barrel portion adapted to be retainingly received in anyone of a plurality of dimples formed in a wall of the passage in said guide tube handle.

4. The camera assembly of claim 1 wherein said camera handle supports control buttons for operating the elongated flexible camera portion.

5. The camera assembly of claim 1 wherein said camera handle supports a joy stick for manipulating the elongated flexible camera portion relative to the camera handle.

6. A selectively positionable camera assembly for use in connection with a guide tube assembly having a guide tube handle portion and at least one guide tube therein, said camera assembly comprising:
    an elongated flexible camera portion sized to operably extend through one of the at least one guide tubes of the guide tube assembly;
    a camera handle operably coupled to said elongated flexible camera portion and being movably supported by at least a portion of the guide tube handle portion; and
    a retainer on at least one of said portion of said guide tube handle and said camera handle for releasably retaining said camera handle in any one of a plurality of orientations relative to said portion of said guide tube handle wherein said camera handle comprises a distal barrel portion that has a series of dimples formed therein, said distal barrel portion being sized to be movably received within a passage in said guide tube handle portion, wherein said retainer comprises at least one spring biased ball detent in said guide tube handle portion for retaining engagement with anyone of said series of dimples, and wherein said series of dimples comprises a plurality of dimples evenly distributed on a perimeter of said barrel portion.

7. A selectively positionable camera assembly for use in connection with a guide tube assembly having a guide tube handle portion and at least one guide tube therein, said camera assembly comprising:
    an elongated flexible camera portion sized to operably extend through one of the at least one guide tubes of the guide tube assembly;
    a camera handle operably coupled to said elongated flexible camera portion and being movably supported by at least a portion of the guide tube handle portion; and
    means for selectively retaining said camera handle in any one of a plurality of axial and circumferential orientations relative to said portion of said guide tube handle.

8. A camera kit for use with a guide tube assembly having a guide tube handle portion and at least one hollow guide tube therein, said camera kit comprising:
    a camera interface adapter coupleable to the guide tube handle portion, said camera interface adapter having a hollow passage extending through;

a camera comprising:
an elongated flexible camera portion sized to operably extend through said hollow passage in the camera interface adapter and one of the at least one guide tubes of the guide tube assembly; and
a camera handle operably coupled to said elongated flexible camera portion and having a distal portion sized to be movably supported within said hollow passage in said camera interface adapter; and
a retainer on at least one of said camera interface adapter and said camera handle for releasably retaining said distal portion of said camera handle in any one of a plurality of axial and circumferential orientations within said passage in said camera interface adapter.

9. The camera kit of claim 8 wherein said camera handle comprises a distal barrel portion that has a series of dimples formed therein, said distal barrel portion being sized to be movably received within a passage in said guide tube handle portion and wherein said retainer comprises at least one spring biased ball detent in said camera interface adapter for retaining engagement with anyone of said series of dimples.

10. The camera kit of claim 8 wherein said camera handle comprises a distal barrel portion that is sized to be movably received within a passage in said camera interface adapter and wherein said retainer comprises at least one spring biased ball detent in said distal barrel portion adapted to be retainingly received in anyone of a plurality of dimples formed in a wall of the passage in said camera interface adapter.

11. The camera assembly of claim 8 wherein said camera handle supports control buttons for operating the elongated flexible camera portion.

12. A camera kit for use with a guide tube assembly having a guide tube handle portion and at least one hollow guide tube therein, said camera kit comprising:
a camera interface adapter coupleable to the guide tube handle portion, said camera interface adapter having a hollow passage extending through;
a camera comprising:
an elongated flexible camera portion sized to operably extend through said hollow passage in the camera interface adapter and one of the at least one guide tubes of the guide tube assembly; and
a camera handle operably coupled to said elongated flexible camera portion and having a distal portion sized to be movably supported within said hollow passage in said camera interface adapter; and
a retainer on at least one of said camera interface adapter and said camera handle for releasably retaining said distal portion of said camera handle in any one of a plurality of orientations within said passage in said camera interface adapter wherein said camera handle comprises a distal barrel portion that has a series of dimples formed therein, said distal barrel portion being sized to be movably received within a passage in said guide tube handle portion, wherein said retainer comprises at least one spring biased ball detent in said camera interface adapter for retaining engagement with anyone of said series of dimples, and wherein said series of dimples comprises a plurality of dimples evenly distributed on a perimeter of said barrel portion.

13. A selectively positionable camera assembly for use in connection with a guide tube assembly having a guide tube handle and a guide tube therein, said camera assembly comprising:
an elongate member sized to operably extend at least partially through the guide tube of the guide tube assembly;
a camera handle operably coupled to said elongate member and being movably supported by at least a portion of the guide tube handle; and
a retainer on one of the guide tube handle and said camera handle for releasably retaining said camera handle in any one of a plurality of orientations relative to the guide tube handle, wherein said retainer is adapted to be retainingly received in anyone of a plurality of dimples formed on said other one of the guide tube handle and said camera handle, and wherein said plurality of dimples are circumferentially distributed on a wall of said other one of the guide tube handle and said camera handle.

14. The camera assembly of claim 13 wherein said plurality of dimples are axially distributed on said wall of said other one of the guide tube handle and said camera handle.

* * * * *